United States Patent [19]

Moll et al.

[11] 4,422,036

[45] Dec. 20, 1983

[54] APPARATUS FOR CONTINUOUSLY MEASURING CELLS OR PARTICLES IN SUSPENSION IN A LIQUID MEDIUM

[76] Inventors: Manfred Moll, Allee Chaptal, Richardmenil, 54630 Flavigny S/Moselle; Jean J. Delorme, 47 bld Albert ler, 54000 Nancy; Jean C. Weber, 16 rue du Portugal, 54500 Vandoeuvre, all of France

[21] Appl. No.: 108,571

[22] Filed: Dec. 31, 1979

Related U.S. Application Data

[63] Continuation of Ser. No. 835,788, Sep. 22, 1977, abandoned.

[30] Foreign Application Priority Data

Aug. 31, 1977 [FR] France .......................... 77 27155

[51] Int. Cl.³ ............................................ G01N 27/00
[52] U.S. Cl. .................................................. 324/71.4
[58] Field of Search .............. 324/71 CP; 73/423 R, 73/425.4 R; 366/140, 142

[56] References Cited

U.S. PATENT DOCUMENTS 3,851,246  11/1974  Curby et al. .................. 324/71 CP
3,979,669   9/1976  Godin ............................ 324/71 CP Primary Examiner—Stanley T. Krawczewicz
Attorney, Agent, or Firm—Robert E. Burns; Emmanuel J. Lobato; Bruce L. Adams

[57] ABSTRACT

An automatic apparatus for measurement of the number of cells or particles in suspension in a liquid medium during fermentation, comprising a preparation unit for the measurement, a measurement receptacle mounted for vertical translation, a device for drawing in the liquid to be measured which is provided with oleopneumatic regulation, electronic circuits and measuring, processing and visualizing members wherein, the active members being connected for their operation to a pneumatic automatic device assuring the completely automatic operation of the assembly.

4 Claims, 9 Drawing Figures

APPARATUS FOR CONTINUOUSLY MEASURING CELLS OR PARTICLES IN SUSPENSION IN A LIQUID MEDIUM

This is a continuation of application Ser. No. 835,788, filed Sept. 22, 1977, now abandoned.

BACKGROUND OF THE INVENTION

This invention relates to an entirely automatically operating apparatus for the automatic taking and preparation of a liquid sample for the determination of the number of cells or particles in suspension in a liquid medium.

A large number of reactions or processes require continuous monitoring of the number of cells or particles present in the operational liquid medium.

There are concerned, for instance, continuous controls of particle size in the production of a product or of the number of cells in suspension in the preparation of a fermented beverage such as beer in which the development of the fermentation phase plays an important role in the quality of the final product.

As a matter of fact, the seed yeast population and its development during the fermentation are considered essential parameters, the value and variations of which must be known.

Thus, the brewing industry has seen the appearance, based on the application of the principle of counting the number of particles which was discovered by Coulter, of an industrial particle-counter which makes it possible to monitor the population during the course of the different phases of the fermentation.

The sampled suspension of yeast, which has been previously diluted in a special electrolyte, is placed in a cylindrical receptacle. This electrolyte forms an electrical resistance between two electrodes, one of which is within a probe which extends into the receptacle and the other outside the said probe within the receptacle.

The probe is immersed in the solution or suspension to be studied. It has a calibrated opening perpendicular to its wall through which the electrolyte and the yeast cells pass, the yeast cells upon each of their passes modifying the electric resistance between the two electrodes, since the conductivity of the particles is different from that of the electrolyte.

As for the peripheral units, they consist essentially of a tube or column of mercury which assures a sufficient vacuum to aspirate a given constant volume of electrolyte out through the measurement orifice; they also comprise visualization and counting members.

As indicated, each pass causes a variation in resistivity of the electric measurement circuit. Each instantaneous variation provides an electric pulse which is electronically counted, whereupon its size is analyzed.

This equipment does great service in breweries; however, its operation still requires a good deal of human intervention, for instance preparation of the electrolyte by a laboratory assistant, no automatic recording of the measurements, etc., and the performance of this apparatus, in view of the degree if automation of the production lines, is inadequate.

SUMMARY OF THE INVENTION

The object of the present invention is to provide an entirely automatic and particularly effective apparatus.

It relates to an apparatus for the continuous measurement of the number of cells or particles in suspension in a liquid medium, comprising a sampling and diluting unit for the formation, with an electrolyte, of the suspension to be studied, a liquid suction and admission device of oleopneumatic action, an ultrasonic treatment block, a pneumatic sequencer for the automatic operation of the unit, a measurement tube of new design, drive members connected with the sequencer, and members for discharge measurement, and processing of the measurement signals.

Due to its entirely automatic operation and its structure, the apparatus in accordance with the invention has numerous advantages, namely:

an automatic dilution sampling circuit which assures the initial operations without human intervention;

presence of an oleopneumatic suction and admission device which does away with the drawbacks of the vacuum unit of the mercury-column type, such as pollution, oxidation, breaking of the column, etc., resulting in a lack of reliability on an industrial scale application;

direct indication and recording of the number of particles, of the mean number, and of the biomass;

measurement tube of new design which avoids the drawbacks formerly encountered, such as clogging and parasitic bubbles;

the measurement beaker is displaced in order not to subject the orifice tube to ultrasonics.

To the indicated field of application there is also added the entire field of continuous granulometry.

BRIEF DESCRIPTION OF THE DRAWING

The invention will be better understood from a reading of the following description of a preferred embodiment of the invention, supplemented by the accompanying drawings, in which.

DESCRIPTION OF THE PREFERRED EMBODIMENT

Figure 1:
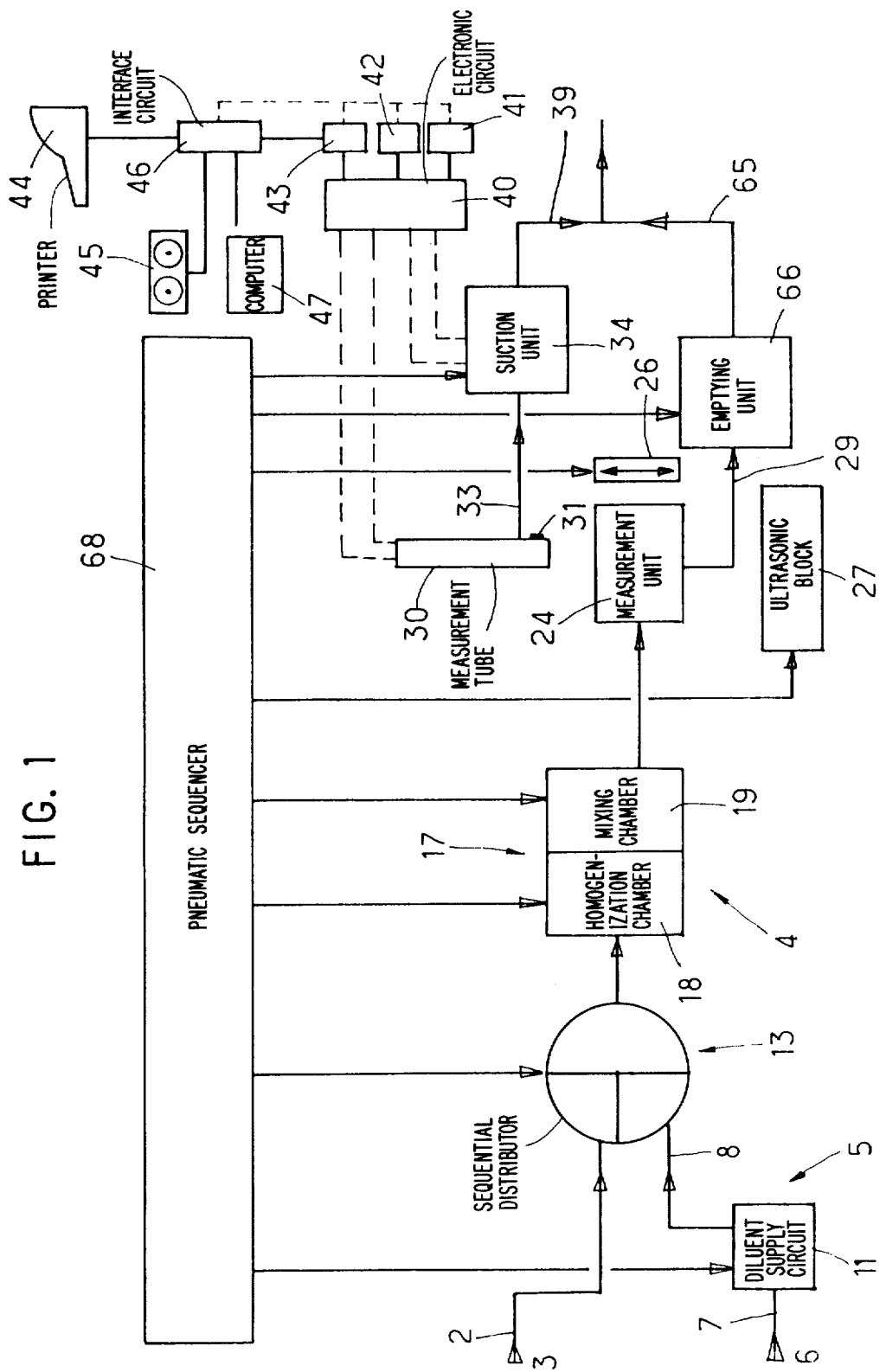
FIG. 1 is a diagram of the internal construction of the apparatus based on functional blocks.

The automatic measuring apparatus in accordance with the invention has, of course, other uses than in a brewery, for instance on fermented liquids or semi-liquids of any kind, and more generally all continuous granulometry measurements.

The measurement preparation unit 1 will first of all be examined. It comprises a conduit 2 for sampling, for instance, beer 3, or other product to be measured coming from the fermentation tank and extending towards the automatic dilution unit 4 described below.

The sampling conduit comes from a sampling circuit which connects it to the fermentation tank, the details of which circuit will be described below in the example of application contemplated.

The circuit 5 for the supply of the diluent 6 which forms the electrolyte is composed of an inlet conduit 7 and a distribution conduit 8 having at the place of their junction a common trunk 9, a double shut-off device 10 with separate action on one and the other branches, for instance of the tube-clamp type.

The common trunk is connected to a double-acting dispenser 11 with piston connected to a drive ram 12 fed with compressed fluid.

The beer and electrolyte circuits lead to a distributer sequential device 13, for instance a sampling valve which assures the successive feeding of representative samples of beer and electrolyte to the automatic dilution unit 4 to which it is connected by a conduit 14.

The distributing device 13 is driven in a backward and forward movement by a double-acting ram 15 which actuates a suitable mechanism 16.

The automatic dilution unit is formed of a double-mixing chamber 17 having two successive compartments—a homogenization chamber such as 18, and a mixing chamber 19 proper, both fed at their upper part in succession at 20 by a filtered fluid under low pressure, preferably filtered air.

The homogenization chamber which is fed tangentially at the level of its cylindrical-conical transition communicates at its bottom with the mixing chamber proper through a conduit 21 which is slightly inclined and arrives tangentially at the location of the transition, the said chamber being provided at its lower level with an evacuation conduit 22 which connects it, via a shut-off device 23, for instance a tube clamp, to the receptacle 24 of the measurement unit 25.

The liquid arriving in the homogenization chamber 18 is subjected to a first mixing due to the injection of air under low pressure in the upper part of the other chamber 19, while the chamber 19 is opened to the air. The homogenizing effect continues by the passage through the communication conduit and its tangential arrival at the conical portion of the chamber where it forms an eddy.

After its transfer into this second chamber, it is subjected to bubbling by the injection of air into the homogenization chamber, before progressing towards the measurement receptacle 24.

The latter is composed of a cylindrical beaker having a pierced conical base. It is attached firmly to a ram mechanism 26 for vertical displacement from an upper measuring position to a lower ultrasonic treatment position on an ultrasonic block 27 controlled by the pneumatic switch 28.

This displacement takes place entirely automatically in accordance with the commands given by the operating automatic machine, namely low position, ultrasonic treatment, high position: measurdetection circuit.

In the high position, during the measurement phase, the mixture is delivered by vacuum to the measurement unit 25 thrugh the orifice tube 30 via a suction device 36 with oleopneumatic regulation via the suction conduit 33 and a backward-forward branch 37 with double closure 38 for the suction conduit 33 and the evacuation conduit 39.

The measurement electrodes are connected to an electronic circuit block 40 for the pick-up of information (detection, forming, etc.) for the voltage pulses caused by the change in resistivity upon the passage of each particle or cell or group of particles.

These data are processed by three electronic circuit blocks connected to the information pick-up block 40. There are concerned:

a multi-channel analyzer 41 which selects the pulses produced from the measurement tube;

an integration block 42 which integrates the pulses to give the mean value of the volume of the particles or cells in suspension;

a pulse counter with coincidence corrector 43 which supplies the total number of cells or particles, weighted by a statistical coefficient which takes into account possible errors due to the simultaneous passing of several cells through the measurement orifice.

One thus has data necessary for the calculation of the biomass, which is equal to the product of the number of particles or cells in suspension by the average volume.

This apparatus comprises a recorder for automatic recording of the above parameters and, in particular, recording of the data of the pulse counter by a printer 44 and a recorder 45, for instance a graphical recorder, which are connected to the electronic blocks by an interface circuit 46 for convenient industrial utilization of the measurements, or coupled to a computer 47.

Figure 4:
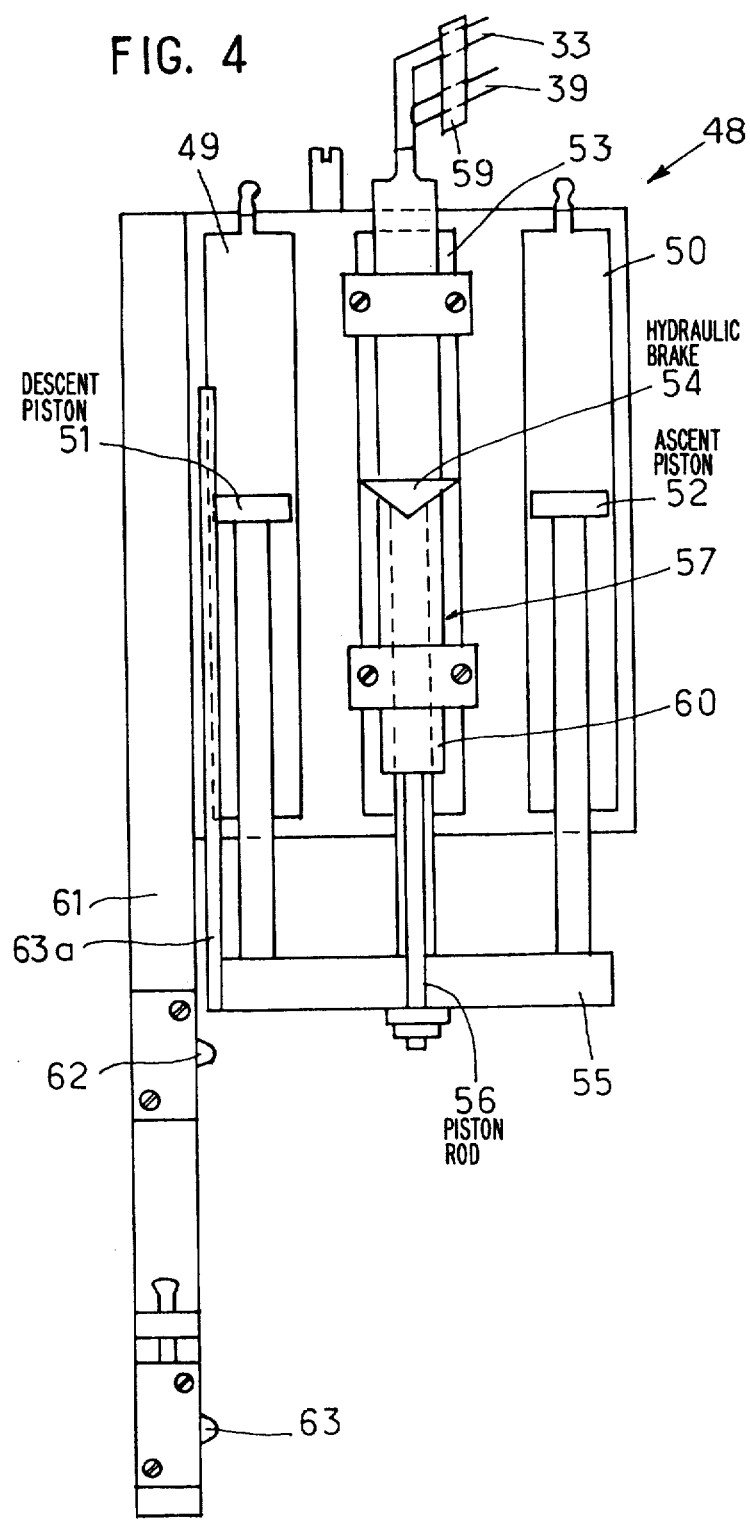
FIG. 4 is a view in elevation of the suction device.

The suction device 36 with oleopneumatic regulation which is provided for the apparatus in accordance with the invention and shown in FIG. 4 consists of a displacement assembly 48 with three branches comprising, on the one hand, at the ends two cylindrical ram bodies 49 and 50 in which there slide respectively the descent piston 51 and ascent piston 52 and, on the other hand, a central cylinder 53 containing a hydraulic brake 54.

The three rods of these sub-assemblies are connected at their bases by a flat plate 55 which is rigidly connected with a piston rod 56, and a dispenser 57 connected to the suction conduit 33 and to an evacuation conduit 39, each via a closure means 59, for instance of the tube-clamp type.

The piston rod 56 together with a cylinder 60, attached mechanically along the displacement assembly, constitutes the suction assembly.

The latter furthermore comprises, in its lengthwise direction, a contact-bearing bar 61 which has two separate contacts 62 and 63 of the end-of-stroke type for the starting and stopping respectively of the counting, which are actuated during the displacement by the front plate 55, as well as a support plate 63a for the contacts.

The regular displacement with adjustable speed of the piston rod of the dispenser downward produces a sufficient vacuum to create a perfectly constant suction, as necessary for the measurement. This results from the great linearity and speed of displacement of the rod caused by the descent of the pistons which are controlled by the hydraulic brake in the suction device.

One thus has a high degree of reliability for the apparatus and a high quality of the measurement.

Figures 2, 3:
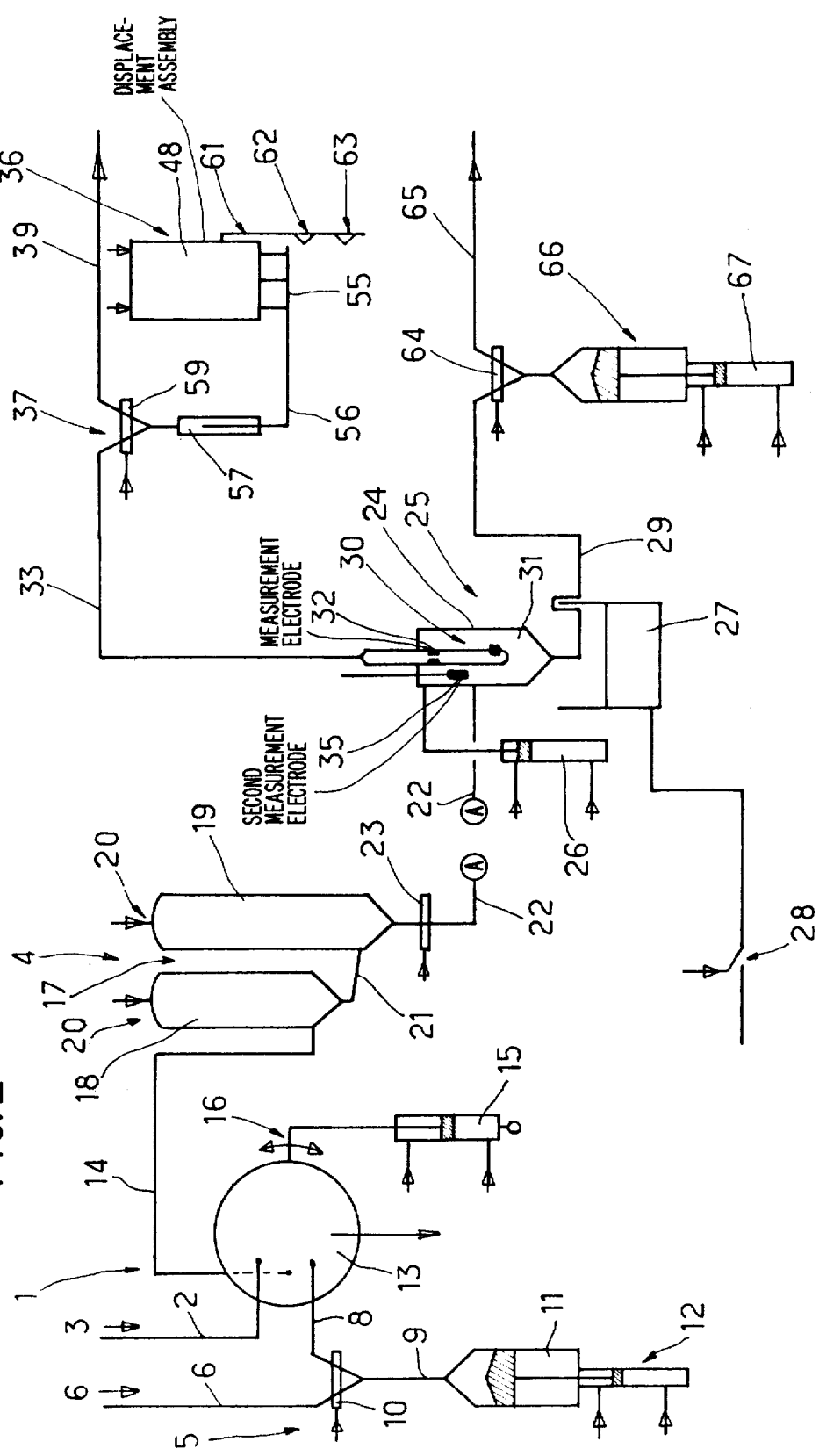
FIG. 2 is a diagrammatic view of the measurement preparation assembly.
FIG. 3 is a diagrammatic view of the measurement circuit with suction and drainage.

The measurement assembly furthermore comprises an emptying circuit (FIG. 3), formed of the discharge conduit 29, a double closure means 64 on the inlet and outlet conduits 65, an emptying dispenser 66 formed of a cylinder-piston assembly actuated by a pneumatic emptying ram 67 which discharges towards the outside for its evacuation through the discharge conduit 65.

The completely automatic operation of this measurement apparatus is assured here by a pneumatic automatic device of the pneumatic sequencer type fed with compressed fluid from the network for its own operation and the driving of the active units and members, namely rams, closure means, operation of the sampling valve, etc.

The same fluid under low pressure serves for the homogenizing of the mixture.

The automation chain consists primarily of a pneumatic sequencer 68 formed, non-limitatively, of fifteen phase modules or control units such as 69 of pneumatic operation which are connected in series and fed at 70 with compressed fluid.

This sequence traversed by phase or step throughout the entire operation organizes the program of a measurement cycle divided into two subprograms corresponding to the measurement and to the rinsing.

These phase modules directly drive the active and measurement members of the apparatus, feeding them for the desired period of time with compressed fluid via circuits or the like such as 71 combining the actions of the phase modules of the first subprogram with those of the second, which are provided for the same members.

The durations of each phase are imposed by timers such as 72 fed with compressed fluid by the phase modules, transmitting to the latter a pneumatic stop signal by zero reset.

Thus the timers, of which there are nine, the first six perform two functions, the control time of operation and the passage to the following process step.

Figure 5:
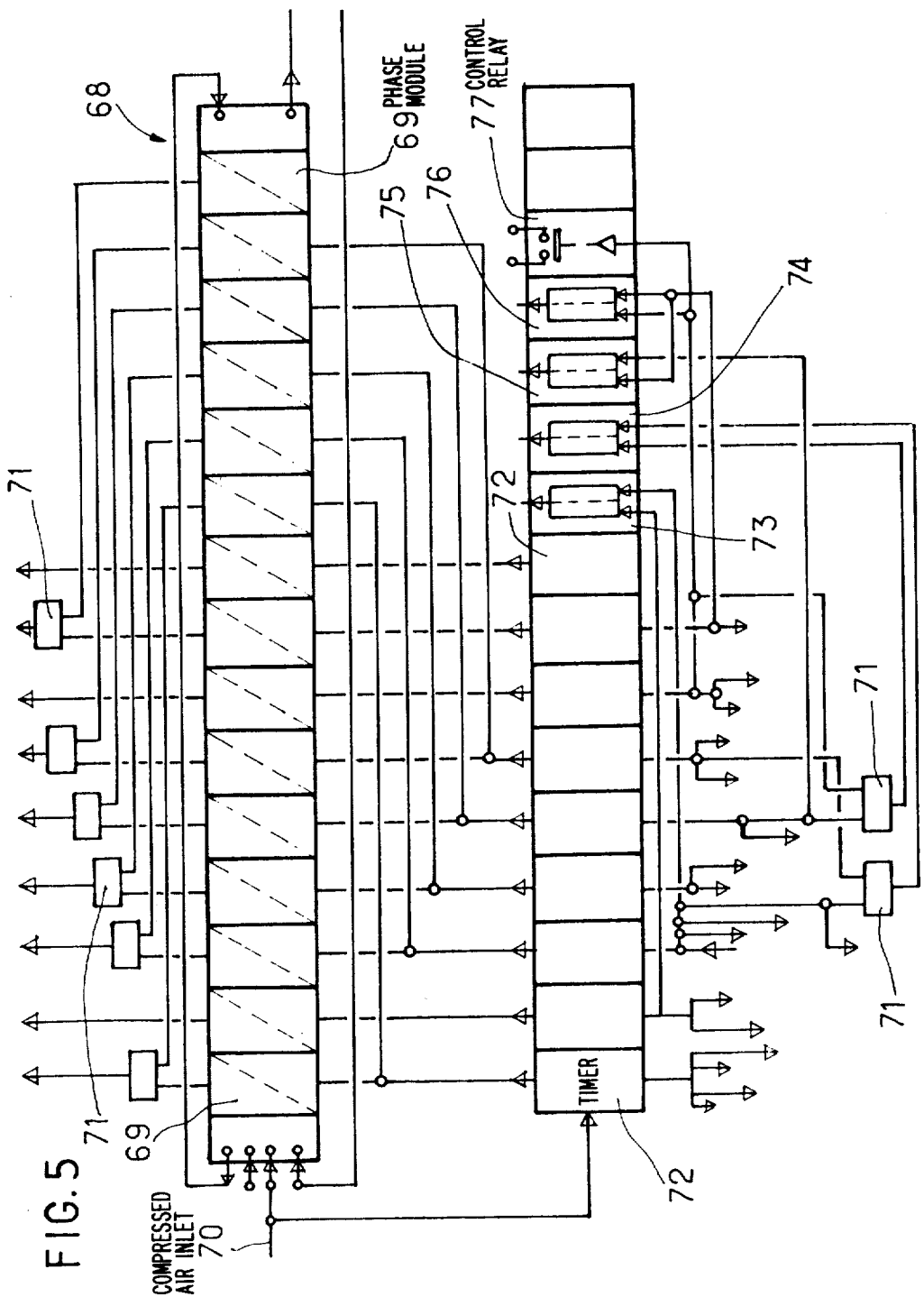
FIG. 5 is a diagram of the sequencer.

Connected with the timers, in accordance with the diagram of FIG. 5, there is provided the operating memories 73 of the sampling valve, 74 of the low-pressure filtered air control in the homogenization chamber and 75 of the mixing chamber via 75, and finally the drive memory 76 for the displacement ram of the measurement receptacle coupled with the drive of the operating contact 77 or control relay of the ultrasonics.

The phase modules, in their turn, actuate the placing in operation or the release of the pistons, the sampling valve, and the ultrasonic block, the sampling valve, the rinsing pass, the transmitting of the mixture pressure, the shutting of the sampling valve, the ascent of the measurement receptacle, etc., in accordance with the diagram shown in FIG. 5.

The automatic operating program takes place in accodance with the following sequences:
sampling of the electrolyte;
sampling of the beer;
pushing of the beer by the electrolyte and mixing;
homogenization of the mixture by filtered low-pressure fluid;
transportation of the sample into the measurement chamber;
descent of the ultrasonic chamber;
treatment of the sample with ultrasonics;
ascent of the measurement receptacle to the level of the orifice tube;
measurement by suction caused by the displacement of the rod of the oleopneumatic assembly;
emptying of the measurement chamber;
rinsing, entailing the same operations with the electrolyte alone;
of course, beer is not admitted into the circuit.

One interesting feature in the operation consists in providing the stopping of the sequence at the phase such that the orifice tube is in the liquid-filled measurement receptacle, thus protecting it from any clogging.

Figure 6:
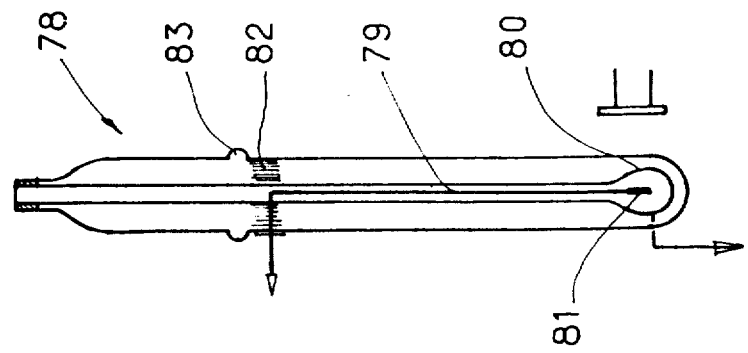
FIG. 6 is a sectional view showing of one interesting embodiment of the mercury tube.

An orifice tube of new design has been provided, which is particularly well-adapted to the continuous operation of the above apparatus, employing the Coulter measurement principle. It is shown in FIG. 6.

It has the shape of an elongated cylindrical bulb 78 of monoblock structure with cylindrical median interior cavity of small diameter 79 and with lower bulb 80 containing the electrode 81 in its upper part.

This electrode is connected to an outer metallization ring 82 preceding a peripheral reinforcement 83.

The bulb opens to the outside via a measurement orifice of a diameter of the order of 100 microns.

This orifice, and more generally this orifice tube, is characterized by its monoblock structure without internal roughnesses which might retain the bubbles and by its widened chamber or bulb into which the orifice opens for a substantial improvement of the flow during the measurement.

One particularly interesting example of use of the apparatus in accordance with the invention consists of the continuous or semicontinuous supervision (case of several tanks or vats in a battery to be supervised), of the fermentation of the beer by effecting multiple measurements of the number of cells in suspension in the liquid during fermentation.

Figure 7:
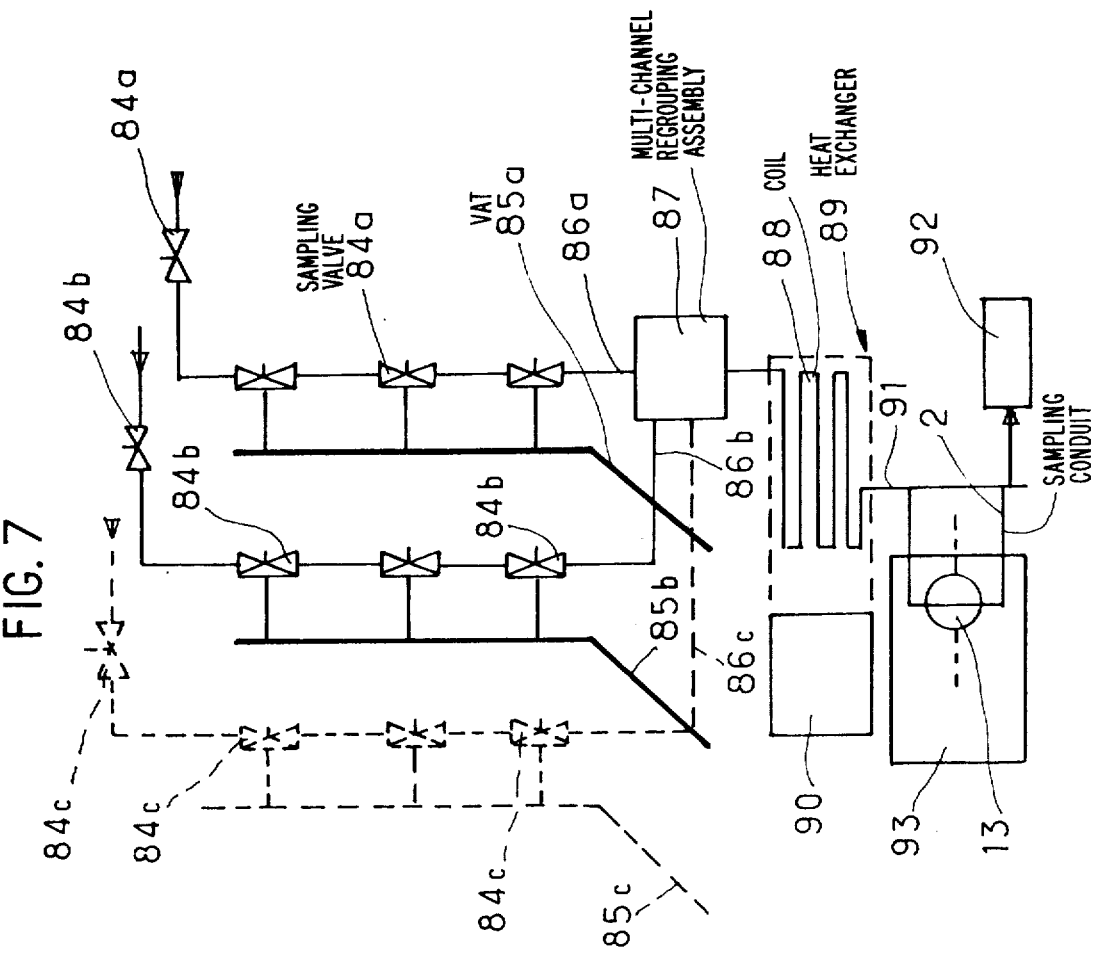
FIG. 7 is a diagrammatic representation of the connecting of the apparatus in accordance with the invention to a continuously operating beer fermentation tank.

The sampling chain shown in FIG. 7 is established based on sampling valves such as 84a, 84b, 84c, located at several levels over the height of a tank (vats 85a, 85b, 85c).

Of course it is possible to simultaneously control this phenomenon developing in several tanks by proceeding with successive analyses, in the same apparatus, of samples corresponding to different tanks.

One then arrives at the installation described in a parallel patent.

There is concerned coupling the series of sampling valves of several fermentation vats to be supervised, by their principal conduit 86a, 86b, 86c in a multi-channel regrouping assembly 87 delivering into the coil 88 of the heat exchanger 89 of a refrigerating group 90, which coil is continued by a section 91 to which there is shunted the sampling circuit 2 of the present apparatus leading to the sampling valve 13.

The said section 91 continues to an assembly 92 for the measurement of other parameters.

The sampling circuit forms part of a block 93 which is, in fact, the apparatus of the invention.

The circuit 46 used in the apparatus of the invention will be described below.

Figure 8A:
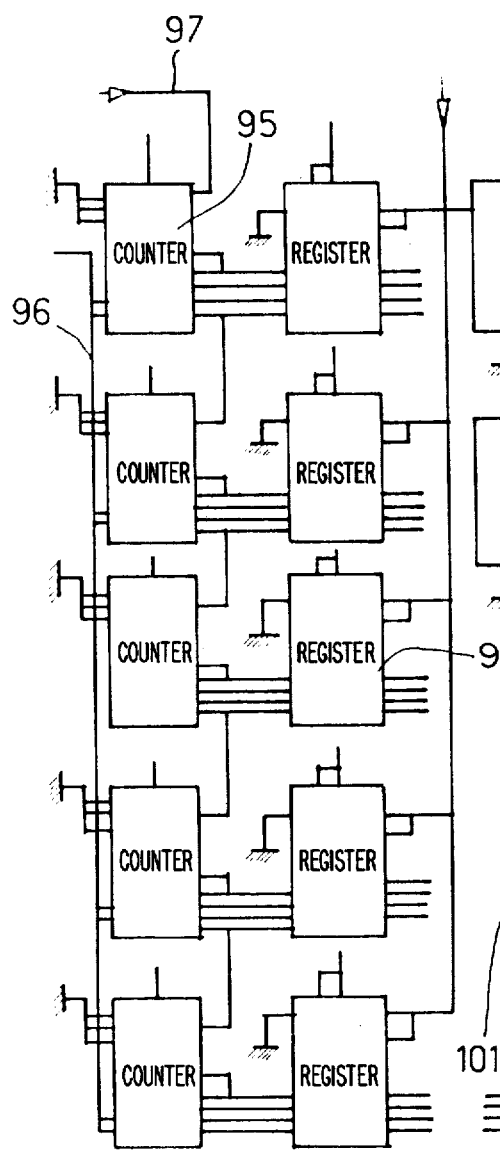
FIGS. 8a and 8b are schematic diagrams of interface circuits.
Figure 8B:
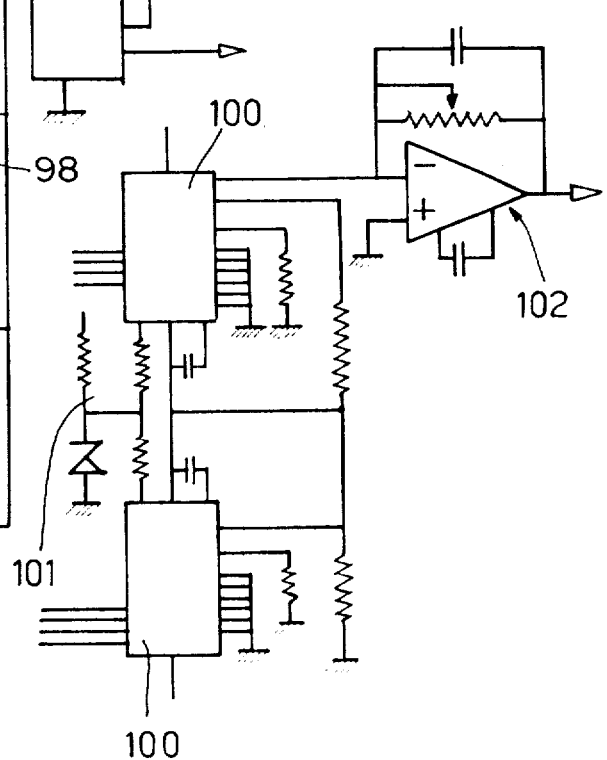

It consists of an interface circuit for a printer (FIG. 8a) and an interface circuit for a tracing table (FIG. 8b).

The first comprises a counting part 94 in the form of a plurality of counters such as 95 connected together in cascade, having a resetting line 96.

The first counter comprises the input 97 of the interface circuit connected to a pulse line for counting pulses from the coincidence corrector 43 after the pulses have been formed. Each saturated counter increments the following one. One thus obtains in BCD code a counting line having a counter for the units, the tens, etc.

Each counter is connected to a register or to a register element such as 98 in which there are recorded the counting data until they are discharged into the printer after transformation of the BCD code into binary code in a transcoder 99.

The tracing table interface is actually a necessary addition to the above interface if a tracing table is to be used, the input of the circuits which such as 100, fed by 101, is connected to the output of the registers corresponding to the most significant numbers (thousands and tens of thousands in the present case).

These circuits take the most significant signal and act on a tracing table via an adaptation circuit 102.

Two important points remain to be made clear:
the sampling valve assures the sampling of the beer in position of flow of the beer in the sampling circuit so as to make certain that the liquid contained in the sampling body is representative of the beer in the course of fermentation and not of the mass of stagnant liquid in the upstream part of the circuit;

a countercurrent rinsing of the orifice after the measurement is provided in order to avoid any trouble when effecting a timed control of the closing of the admission conduit 33 upon the advance of the piston rod of the dispenser 57.

The invention has been described in detail, but it will be understood that it is not limited to the elements of the above description, which has been given on basis of an illustrative embodiment, but rather the invention covers all variants.

We claim:

1. An automatic apparatus for sampling and preparing a sample of a liquid medium during the course of fermentation of the liquid medium and for determining the number of cells or particles in suspension in the liquid medium, said apparatus comprising:

sampling means for sampling a liquid medium;

dilution means for diluting the sample of liquid medium;

measuring means for measuring the number of cells or particles in the diluted sample of liquid medium;

said measuring means comprising a measurement receptacle for containing the diluted sample of liquid medium and being positionable at a raised measurement position and a lowered treatment position, ultrasonic applicator means for applying ultrasonic energy to the diluted sample of liquid medium within said measurement receptacle when said measurement receptacle is in the lowered treatment position, a measurement electrode positioned for measuring the number of cells or particles in suspension in the diluted sample of liquid medium within said measurement receptacle when said measurement receptacle is in the raised measurement position; and sequential actuating means for automatically sequentially actuating said sampling means, said dilution means and said measuring means to sequentially sample, dilute, treat with ultrasonic energy and measure the liquid medium.

2. An automatic apparatus according to claim 1, wherein said sampling means and said dilution means together comprise a conduit for receiving the liquid medium, a source of diluent, a mixing chamber for mixing the liquid medium and the diluent, and means for sequentially alternately delivering predetermined samples of liquid medium and predetermined quantities of diluent for diluting the predetermined samples of the liquid medium.

3. An automatic apparatus according to claim 2, wherein said mixing chamber is a double mixing chamber comprised of a pair of generally vertical chambers having vertical sidewalls and conical converging bottom walls intersecting the sidewalls and converging downward to define outlets of the pair of chambers, each of said chambers having an inlet at the intersection of its sidewall and bottom wall, a conduit from the outlet of a first of said chambers to the inlet of a second of said chambers with the inlet of said second chamber lower than the outlet of said first chamber, and means for introducing filter fluid under low pressure into said chambers at upper end portions thereof.

4. An automatic apparatus according to claim 1; wherein said sampling means, said dilution means and said measuring means are fluid actuated; and wherein said sequential actuating means is effective for developing fluidal actuating signals for actuating said sampling means, said dilution means and said measuring means.

* * * * *